United States Patent [19]

Patel et al.

[11] Patent Number: 4,886,660

[45] Date of Patent: Dec. 12, 1989

[54] SHINE HAIR CONDITIONER

[75] Inventors: Amrit Patel, Dayton; Frank Schebece, Edison, both of N.J.; Harry Greenland, Wahroongha, Australia

[73] Assignee: Colgate-Palmolive Company, Piscataway, N.J.

[21] Appl. No.: 62,032

[22] Filed: Jun. 11, 1987

[51] Int. Cl.$^4$ .......................... A61K 7/08; A61K 7/06
[52] U.S. Cl. ........................... 424/70; 424/71; 424/DIG. 2; 514/880; 514/881
[58] Field of Search ..................... 424/70, 71

[56] References Cited

U.S. PATENT DOCUMENTS

| | | | |
|---|---|---|---|
| 3,068,151 | 8/1962 | Haefele | 435/294 |
| 3,144,391 | 5/1964 | Goff | 424/47 |
| 3,216,983 | 3/1965 | Shelanski et al. | 525/60 |
| 3,579,629 | 2/1971 | Pasero et al. | 424/47 |
| 3,697,644 | 2/1972 | Laiderman | 424/70 |
| 3,808,051 | 1/1974 | Sato et al. | 134/2 |
| 3,876,760 | 9/1975 | Nersesian et al. | 424/70 |
| 3,925,542 | 12/1975 | Viout et al. | 424/70 |
| 3,928,558 | 11/1975 | Cheesman et al. | 424/47 |
| 3,959,461 | 7/1976 | Bailey et al. | 424/70 |
| 3,959,463 | 6/1976 | Nersesian | 424/70 |
| 4,144,326 | 5/1979 | Luedicke, Jr. et al. | 424/70 |
| 4,160,823 | 6/1979 | Watanabe et al. | 424/70 |
| 4,165,369 | 11/1979 | Watanabe et al. | 424/70 |
| 4,183,917 | 3/1980 | Iwao et al. | 424/70 |
| 4,210,161 | 7/1980 | Wagman | 424/70 |
| 4,220,166 | 5/1980 | Newell | 132/209 |
| 4,269,824 | 10/1981 | Villamarin et al. | 424/70 |
| 4,311,695 | 2/1982 | Starch | 424/70 |
| 4,374,825 | 8/1983 | Bolich et al. | 424/70 |
| 4,387,090 | 9/1983 | Bolich | 424/70 |
| 4,389,418 | 11/1983 | Burton | 514/785 |
| 4,421,740 | 10/1983 | Burton | 424/70 |
| 4,436,722 | 4/1984 | Matsunaga et al. | 424/70 |
| 4,472,375 | 1/1984 | Bolich et al. | 424/70 |
| 4,493,824 | 9/1985 | Abe | 424/70 |
| 4,610,874 | 2/1986 | Matravers | 424/70 |
| 4,725,433 | 2/1988 | Matravers | 424/70 |
| 4,818,523 | 4/1989 | Clarke et al. | 424/70 |

FOREIGN PATENT DOCUMENTS

| | | | |
|---|---|---|---|
| 7799887 | 4/1987 | Australia . | |
| 731508 | 4/1969 | Belgium . | |
| 727588 | 2/1966 | Canada | 167/73 |
| 134998 | 10/1984 | European Pat. Off. . | |
| 0134998 | 3/1985 | European Pat. Off. . | |
| 155806 | 11/1985 | European Pat. Off. . | |
| 1402017 | 10/1965 | France . | |
| 889291 | 2/1962 | United Kingdom . | |
| 1540862 | 2/1979 | United Kingdom . | |

OTHER PUBLICATIONS

Smith, L. R. and Weinstein, M., "Clear Hair Rinses," Apr. 1977, pp. 50, 52, *Soap/Cosmetics/Chemical Specialties.*

Scott, et al., *Sorption of Quaternary Amonium Surfactants by Human Hair,* J. Soc. Cosmetic Chemists, 20, 135–152, (Feb. 5, 1969).

*Primary Examiner*—Ronald W. Griffin
*Attorney, Agent, or Firm*—Richard J. Ancel; Robert C. Sullivan; Murray M. Grill

[57] ABSTRACT

A stable shine hair conditioner formulation which provides shiny, smooth, manageable hair, easy to comb, easy to style, long holding power and is cost effective consisting essentially of effective amounts of $C_{14}$–$C_{22}$ alkyl trimethyl quaternary ammonium compound, mineral oil or glyceryl monostearate, a $C_{14}$–$C_{22}$ alkanol, a cellulose polymer, a copolymer of polyvinylpyrrolidone and vinyl acetate (PVP/VA) and a plasticizer selected from the group consisting of lanolin acetate, propylene glycol, glycerine, and water soluble lanolin, in an aqueous vehicle.

14 Claims, No Drawings

SHINE HAIR CONDITIONER

FIELD OF INVENTION

The present invention relates to a novel shine hair rinse conditioner which provides maximized shine, manageability, ease of styling and long holding power, and is cost effective. The essential components of this composition are $C_{14}$-$C_{22}$ alkyl trimethyl quaternary ammonium compound, a $C_{14}$-$C_{22}$ alkanol, a mineral oil or glyceryl monostearate, a cellulose polymer, a PVP/VA copolymer and a plasticizer such as propylene glycol, lanolin acetate and the like, in an aqueous medium.

BACKGROUND AND PRIOR ART

When hair is washed with modern shampoos it is usually cleaned very efficiently, and the process not only removes soil, but also tends to remove the natural sebum which serves to lubricate the hair. This removal of lubrication increases the friction between the individual hair fibers and promotes tangling, both in wet and dry hair. It also gives rise to a build-up of static charge on the hair, particularly from interactions with plastic combs and hair brushes. The net result is damage to the hair. Also damage to the outer surface of hair is a continuous process caused by such factors as washing, brushing, atmospheric influences, etc. This continuing damage is very much associated with surface friction and any influences to reduce friction and static charge will also reduce the amount of damage to the hair.

The absorption onto hair of quaternaries having long chain fatty portions as part of its molecule is the basis for most hair conditioner formulae. The fatty portion of the molecule, which is largely attached to the substrate, acts as a lubricant. The lubricating action makes combing easier. However, this substantivity of said quaternary compounds to the hair dulls the hair and builds up on the hair.

It has been found that present novel conditioners reduce the inter-fiber friction in the hair, neutralize any static charge build-up on the hair, and provide an exceptional shine to the hair.

In the field of hair conditioning, the prior art is replete with hair conditioning compositions containing one or more of the components of the present novel and unique shine hair conditioner compositions. For example, U.S. Pat. No. 4,160,082 discloses compositions containing a stearyltrimethyl ammonium chloride conditioning agent and propylene glycol. U.S. Pat. No. 4,210,161 discloses a creme rinse containing cetyl trimethyl ammonium chloride and hydroxyethyl cellulose thickening agent. In U.S. Pat. No. 4,421,740, a conditioning composition is disclosed which employs the combination of a mixed higher alkyl $C_{12}$-$C_{18}$ trimethyl ammonium chloride, cetyl or stearyl alcohol and hydroxyethyl cellulose. U.S. Pat. No. 4,436,722 discloses the combination of cetyl trimethyl ammonium chloride, cetyl alcohol and propylene glycol in hair conditioning compositions. U.S. Pat. No. 4,144,326 discloses an oil free hair rinse composition which includes the quarternary ammonium compound combination of lauryl trimethyl ammonium chloride and dialkyl dimethyl quarternary ammonium chloride or bromide, along with propylene glycol and hydroxypropylmethyl cellulose acidified with citric acid. U.S. Pat. No. 4,183,917 discloses an oil-in-water emulsion hair conditioning composition which comprises the combination of $C_{10}$-$C_{22}$ alkyl trimethyl ammonium chloride, mineral oil, cetyl alcohol and propylene glycol. U.S. Pat. No. 4,530,830 discloses a hair relaxer composition containing the combination of a higher alkyl trimethyl ammonium hydroxide in an amount of 2.5-10% by weight as a hair relaxer, cetyl or stearyl alcohol, mineral oil and propylene glycol. U.S. Pat. No. 3,928,558 discloses a hair spray composition containing cyclomethicone and a copolymer of vinyl pyrrolidone and vinyl acetate (PVP/VA) in a methylene chloride/isopropyl alcohol mixture. British Patent No. 1,540,862 discloses that PVP/VA copolymers form an undesirable brittle film on the hair which causes unpleasant dusting and a dandruff-like condition, and are difficult to rinse off the hair.

However, it is noted that none of the above cited patents discloses a hair conditioner composition comprising the specific mixture of a $C_{14}$-$C_{22}$ alkyl trimethyl ammonium halide, a $C_{14}$-$C_{22}$ alcohol, mineral oil or glyceryl monostearate, a cellulose polymer, PVP/VA, and a plasticizer such as lanolin acetate, glycerine, water soluble lanolin or propylene glycol as the essential ingredients emulsified in an aqueous medium.

SUMMARY OF THE INVENTION

It has been found that a shine hair rinse conditioning composition comprising the mixture of $C_{14}$-$C_{22}$ alkyl trimethyl ammonium compound, a copolymer of polyvinylpyrrolidone and vinyl acetate, a $C_{14}$-$C_{22}$ alkanol, mineral oil or glyceryl monostearate, a nonionic water soluble cellulose polymer, and propylene glycol or lanolin acetate, dispersed in an aqueous medium provides a stable composition having excellent conditioning properties, including high luster or shine, combability, static control, ease of styling of the hair and long lasting power.

Accordingly, a primary object of the present invention is to provide a hair rinse conditioner which imparts a superior shine to the hair.

Another object of present invention is to provide a rinse conditioner which imparts superior conditioning effects, softness and manageability, static control, ease of combing and styling and long holding power.

Another object of the present invention is to provide a stable, non-irritating, rinse conditioner capable of being applied daily after shampooing.

Another object of the present invention is to provide an economical hair rinse conditioner containing a minimum concentration of essential active ingredients.

Additional objects, advantages and novel features of the invention will be set forth in part in the description which follows, and in part will become apparent to those skilled in the art upon examination of the following specification or may be learned by practice of this invention.

To achieve the foreoing and other objects and in accordance with the present invention as embodied and broadly described herein, the novel shine hair conditioner composition of this invention consists essentially of about 0.375% to 2.5% by weight of a $C_{14}$-$C_{22}$ alkyl trimethyl quaternary ammonium compound, about 0.25 to 2.5% by weight of a nonionic water soluble cellulose polymer, about 1% to 10% by weight of a $C_{14}$-$C_{22}$ alkanol, about 0.2% to 1.5% by weight mineral oil or glyceryl monostearate, about 0.1% to 1.0% by weight of a copolymer of polyvinylpyrrolidone and vinyl acetate, and about 0.2% to 2% by weight of a plasticizer selected from the group consisting of lanolin acetate, water soluble lanolin, glycerine and propylene glycol, in about 80% to 97.5% by weight of an aqueous carrier. The final product is in the form of an emulsion and has a pH of about 2.5 to 4.5 and preferably 2.7 to 4.3.

In a preferred aspect, the present invention relates to a stable high shine hair conditioner composition having a pH of about 2.5 to 4.5 consisting essentially of, by weight, about 0.375% to 2% of a $C_{14}$–$C_{22}$ alkyl trimethyl halide, and a $C_{14}$–$C_{22}$ alkanol in the ratio of about 1 to about 5, about 0.25 to 2% of a nonionic water soluble cellulose polymer, about 0.2 to 0.5% PVP/VA, about 0.3% to 1.0% mineral oil or glycerol monostearate, about 0.2% to 1.5% of propylene glycol or lanolin acetate, and about 0.2–1% of cyclomethicone as a preferred additional ingredient, dispersed in 89% to 96% of deionized water.

The described hair conditioner compositions are stable, opaque liquids at room temperature having a viscosity of about 4,000 to 12,000 cps and a minimum specific gravity of 0.990. Further, these compositions are stable at 5 degrees C. to 60 degrees C. These compositions are oil-in-water emulsions, with the quaternary compound, the alkanol and the sineral oil supporting the emulsification properties and product stability.

As indicated, these compositions contain safe chemicals which are not irritating to the skin, are non-toxic and are effective to provide a high shine to the hair and improve the manageability of the hair. The PVP/VA copolymer and the water soluble nonionic cellulose polymer (hydroxyethyl cellulose) maximize the shine effect. These polymer films are plasticized by the lanolin acetate or the propylene glycol to obtain shiny, smooth, manageable hair.

The good conditioning properties are imparted to the hair when the composition is applied to the hair with or without subsequent rinsing due to the use of the essential mixture of conditioning agents, namely the $C_{14}$–$C_{22}$ alkyl trimethyl quaternary compound, the $C_{14}$–$C_{22}$ saturated alkanol and the mineral oil or glycerol monostearate. The mineral oil also provides ease of combing as well as luster on the surface of the hair. The glycerol monostearate emulsifies the excess amount of oil on the surface of the oily hair. The viscosity and stability of the hair conditioner is controlled by the quaternary compound and the $C_{14}$–$C_{22}$ alkanol.

DETAILED DESCRIPTION OF THE INVENTION

The long chain mono-higher alkyl quaternary salts which are one of the essential compounds in the mixture of conditioning agents have been used in the prior art as hair conditioning agents. They are water soluble cationic surfactants. Generally, these suitable cationic quaternary ammonium salts have the following formula:

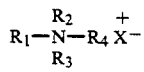

wherein one of $R_1$, $R_2$, $R_3$, and $R_4$ is a long chain alkyl group having 14–22 carbon atoms and the other R groups are each methyl groups; and X is a halide anion anion selected from the group consisting of chloride and bromide. The long chain alkyl group may be a mixture of higher alkyl groups containing 14 to 22 carbons. Representative examples of quaternary ammonium salts include stearyl trimethyl ammonium chloride or bromide, tetradecyl trimethyl ammonium bromide or chloride, cetyltrimethylammonium chloride or bromide and the like.

The mono $C_{14}$–$C_{22}$ alkyl trimethyl quaternary ammonium salts used in the present hair conditioning compositions may be obtained from a number of suppliers either in the form of a liquid or paste in an aqueous and/or isopropanol solvent, or in the form of a solid. For example, the cetyl trimethyl ammonium chloride purchased from Armak, as a 25% active, clear, yellowish liquid in isopropanol contains 25% A.I. (active ingredient) under the tradename Arquad 16-25 W. The mono $C_{14}$–$C_{22}$ alkyl trimethyl ammonium salt is used in an amount of about 0.375 to 2.5% preferably 0.375 to 2%, by weight of the composition.

The second compound in the mixture of conditioning agents is a $C_{14}$–$C_{22}$ alkanol. Since the preferred alkanols are obtained from fats and oils, these alkanols are often referred to as fatty alcohols. However, alkanols made by synthetic processes also are satisfactory. Examples of suitable alkanols are 1-tetradecanol, 1-hexadecanol, 1-heptadecanol, 1-octadecanol and mixtures of $C_{14}$–$C_{22}$ alkanols obtained by hydrogenating the fatty acids derived from tallow. Preferred higher alkanols are stearyl alcohol and cetyl alcohol and mixtures thereof. The proportion of $C_{14}$–$C_{22}$ alkanol present in the conditioner composition is about 1% to 10%, preferably 1.5% to 4%, by weight. Furthermore, the $C_{14}$–$C_{22}$ alkanol usually is the predominant compound in the mixture of conditioning agents because it is present in the largest percentage. Preferably, the weight ratio of $C_{14}$–$C_{22}$ alkanol to the quaternary surfactant is 5:1 because it has been determined that this ratio delivers maximum shine to the surface of the hair for normal hair conditioners, oily hair conditioners, and dry hair conditioners. $C_{14}$–$C_{22}$ alkanols function as co-emulsifying agents, thicken the emulsion, and stabilize the product.

The third essential compound in the mixture of hair conditioning agents is mineral oil for the normal and dry hair conditioning compositions, and glyceryl monostearate for the oily hair conditioner. Mineral oil is a homogeneous mixture of saturated aliphatic and alicyclic hydrocarbons derived from petroleum. Mineral oil is chemically and biologically inert and is hydrophobic in nature. Mineral oil is available in various viscosities. The proportion of mineral oil or glyceryl monostearate present in the hair rinse conditioner composition is about 0.2% to 1.5%, preferably 0.3% to 1.0%, by weight. Usually, the mineral oil or glyceryl monostearate represents less than 15% by weight of the mixtures of the three conditioning agents and preferably less than 10% by weight of said mixtures. Such controlled small amounts of mineral oil tend to counteract the dulling effects of the cationic surfactant by enhancing the shine of the hair and lubricating the hair. Further, the mineral oil assists in decreasing the amount of quaternary salt residue in the hair after shampooing. The glyceryl monostearate will emulsify the excess amount of oil on the surface of the oily hair. In the oily hair conditioer, the combination of glyceryl monostearate and cyclomethicone reduce the oiliness on the surface of the hair. While the glyceryl monostearate emulsifies the excess oil on the hair at the same time the cyclomethicone dries the hair as it volatilizes.

Another essential ingredient in the shine hair conditioning compositions is a water-soluble, nonionic, cellulose polymer which functions both as a thickening agent and as a film forming agent. Suitable cellulosic polymers are selected from the group consisting of hydroxyethyl cellulose and hydroxypropyl methyl cellulose, with hydroxyethyl cellulose being preferred. Hydroxyethyl cellulose is the product of reaction between an alkali cellulose and ethylene oxide, and such products are available in a number of viscosity grades. Viscosity is primarily dependent upon the viscosity of the cellulose used in the reaction. The degree of substitution of hydroxyethyl groups per glycose unit is 1.4–1.5, the hydroxyethyl molar substitution is 1.5–3.0, and these hydroxyethyl celluloses have an average molecular weight range from about 80,000 to about 900,000. A particularly preferred hydroxyethyl cellulose is available under the tradename Natrosol 250 HR from Hercules, Inc. Water-soluble hydroxypropyl methyl cellulose has a methyoxy content between about 25% and about 32% by weight and a hydroxypropyl content between about 2% and 10%, preferably 2% to 7%, by weight. Again, the chain length of the cellulose used in the reaction can be controlled to provide a molecular weight which yields a viscosity for a 2% solution in water in the range of 10 cps and 5000 cps, preferably 50 cps to 4000 cps.

These cellulose polymers provide stability to the cmposition upon aging by viscosity control. The composition retains its viscosity without thinning out or thickening. In addition to controlling the viscosity of the aqueous hair conditioner composition, the cellulose polymer contributes to the shine properties by forming a film on the hair. It appears that this nonionic cellulose cooperates with the other film forming polymer (PVP/VA) to form a polymer film on the hair which maximizes the shine on the hair. The resultant polymer films are plasticisized to obtain shiny, smooth, manageable hair. The proportion of nonionic cellulose polymer is about 0.25% to 2.5%, preferably 0.25% to 2.0%, by weight of the hair conditioner composition.

The other essential film forming polymer in the hair conditioner composition is a water soluble, nonionic copolymer of polyvinylpyrrolidone and vinyl acetate. This PVP/VA copolymer has a specific affinity for the hair and the films formed thereon are generally adhesive, transparent, hard, lustrous and water-rewettable. PVP/VA is commercially available in proportions of 70/30, 60/40, 50/50, 45/55, and 30/70. Other PVP/VA copolymers include 20 to 60% PVP and 40 to 80% VA, commercially available as Luviskol 37E and Luviskol 281 (20% PVP and 80% VA). Polyvinylpyrolidone/vinyl acetate is available in the form of a powder (contains about 95% of polymer and 5% water) and in the form of an aqueous solution. It is believed that the polyvinylpyrrolidone/vinyl acetate cooperates with the cellulose polymer to form a shiny, clear, substantially stiff film on the hair which retains the shape of the hair, and the plasticized film is smooth and pliable so that it does not interfere with combing. The amount of PVP/VA is about 0.1 to 1%, preferably 0.2% to 0.5%, by weight of the final composition. Also, the PVP/VA usually is a lesser amount of the mixture of polymers, so that a smooth, substantially non-tacky film is obtained. Amounts of PVP/VA in excess of 1% by weight yield a film which is too rigid and too tacky.

The film formed by the coaction of the PVP/VA with the nonionic cellulose polymer is plasticized by a suitable plasticizer, preferably selected from the group consisting of propylene glycol, lanolin acetate, glycerin, and water soluble lanolin. The plasticizers are liquids having a low vapor pressure at room temperature. The plasticizers modify the flow properties of the polymers, reduce moisture evaporation, and impart flexibility and toughness to the polymer film. A preferred plasticizer, propylene glycol, is a clear, viscous, colorless liquid which is hygroscopic and is completely miscible with water. Propylene glycol can penetrate both the polymer film and the hair shaft and remain there after rinsing. The effect of this material is believed to result in a softening and swelling of the polymer film and the hair as well as providing a humectant effect to the film, i.e., it enables the PVP/VA -cellulose polymer film to retain its moisture and flexibility between shampooings. Another preferred plasticizer is lanolin acetate, commercially known as Solulan 98 provided by the Amerchol Company. The amount of plasticizer used in the final composition is about 0.2% to 2%, preferably 0.2% to 1.5% by weight.

The final essential ingredient in the shine hair rinse conditioner composition is an aqueous medium which is primarily water, preferably deionized water. Since some of the $C_{14}$–$C_{22}$ alkyl trimethyl quaternary salts may be supplied in admixtures with a $C_2$–$C_3$ alcohol, e.g. isopropanol, the aqueous medium may contain a small amount of said $C_2$–$C_3$ alcohol. Further, if desired, additional amounts of $C_2$–$C_3$ alkanol may be added to the composition, particularly where the composition is sold in the form of a "mousse." The proportion of the aqueous medium is in the range of 80% to 97.5%, preferably 89% to 96%, most preferably 90% to 95.0%, by weight of the hair rinse composition.

An optional component is cyclomethicone which is a volatile cyclic silicone represented by the formula:

wherein R is a $C_1$–$C_3$ alkyl group or a phenyl group, preferably a methyl group; n is a number from 3 to 10, preferably 3 to 7, and the unsatisfied valencies on the oxygen and silicon atoms at the end of the chain are joined together to form a cyclic structure. Suitable cyclic silicones are available as low viscosity fluids from a number of manufacturers, including the General Electric Company. The most preferred cyclomethicones are decamethyl cyclopentasiloxane (General Electric's Silicone Fluid SF 1202) and octamethyl cyclotetrasiloxane (General Electric's Silicone Fluid SF 1173).

The cyclic silicones are non-polar, insoluble in water and completely miscible in lower alcohols, aliphatic aromatic solvents and halogenated hydrocarbon solvents. This ingredient facilitates the distribution of the mixture of conditioning agents on the hair and the quick spreading of the film of conditioners on the hair, and helps quick drying of the hair. The amount of volatile cyclic silicone in the hair conditioner composition is about 0.1% to 2%, preferably 0.2% to 1.0% by weight.

The pH of the shine hair conditioner of present invention is acidic and ranges from about 2.5 to 5.5, preferably about 2.7 to 4.5. Suitable acids which may be used when needed are citric acid and the like.

The coaction of all the seven aforedescribed essential components unexpectedly provides a uniquely superior hair shine conditioner product which is non-irritating. The omission of a single component adversely affects the unique properties of the total composition. Accordingly, the criticality of all seven ingredients and the specificity of each ingredient is necessary in the formulation of the present novel hair shine product. Furthermore, the present hair rinse conditioning composition not only provides an exceptional shine to the hair but also provides body, easy styling, very good curl retention, and good wet and dry combing properties to the treated hair, and is more economical due to the use of minimal amounts of the active ingredients (i.e. cost effective).

The hair conditioner compositions of this invention also may contain conventional additional components such as coloring agents, perfumes, preservatives such as formaldehyde (formalin) and brighteners, such as Uvinul. If the final product is filled into clear bottles, it has been found that the minimum amount of Uvinul necessary to obtain a color stabilized product is 0.02% by weight and up to 0.04% Uvinol. The use of opaque bottles does not require the presence ofo a brightener. The total weight of these optional additives usually does not exceed 5% by weight of the composition and preferably does not exceed 3% by weight of the composition, with the proportion of the individual ingredients often being 1% by weight or less.

The hair conditioner in accordance with the invention may be in the form of a pourable lotion or a smooth cream. Further, the final product may have any suitable viscosity so long as it is appropriate for the final form selected, e.g., a pourable lotion, a thick or viscous lotion or a cream.

The present hair shine conditioner compositions can be manufactured readily by simple mixing methods. For example, a preferred method of preparing the present compositions comprises the steps of dispersing the cellulose polymer (hydroxyethyl cellulose) in about one half of the formula amount of water and mixing while heating to 80-85 degrees C. until a uniform, clear, lump-free solution is obtained; adding the color solution (if used), the $C_{14}-C_{22}$ alkyl trimethyl quaternary ammonium compound and an acid to adjust pH if necessary (citric acid) in sequence with mixing while maintaining the temperature at 80-85 degrees C. to form a uniform aqueous solution; forming a separate mixture of the water-insoluble ingredients, $C_{14}-C_{22}$ alkanol, and the mineral oil or glycerol monostearate and cyclomethicone, when used, and heating said mixture to a temperature of about 80-85 degrees C.; adding the mixture of water-insoluble ingredients to the aqueous mixture with slow agitation; adding the remainder of the water with agitation which cools the resultant emulsion to about 50 degrees C.; adding the PVP/VA and the lanolin acetate or propylene glycol plasticizer to the emulsion at about 50 degrees C.; cooling the resultant emulsion to 39 degrees C. with slow agitation; adding any optional ingredients such as perfume and formalin to the foregoing mixture; and cooling the resultant composition to 25 degrees C. to 30 degrees C. in the presence of slow agitation to form a stable, opaque emulsion having a pH in the range of 2.5 to 5.5 The final product is filled into opaque or translucent containers.

If a clear container is used, at least .02% and up to 0.5% Uvinol brightener is added to the formulation to prevent discoloration of the product.

The use of about one half of the formula amount of water at the end of the mixing process, decreases the cooling time, which speeds up the production and shortens the manufacturing time and saves energy. The use of the total amount of water at the beginning of the process takes a longer period of time to produce the formulation and uses more energy in the cooling operation, and is more costly.

The following examples merely illustrate the invention, but it is understood that the invention is not limited thereto. All amounts of various ingredients in the examples and elsewhere in the specification are by weight unless otherwise specified.

EXAMPLE 1

| Shine Hair Conditioner | AI %(1) |
| --- | --- |
| Deionized Water | Q.S. |
| Cetyl Trimethyl Ammonium Chloride (CTAC) | 0.500 |
| Citric Acid (use as required to adjust pH 3.7 to 4.3) | 0.010 |
| Hydroxyethylcellulose (Natrosol 250 HR) | 1.000 |
| Cetyl Alcohol | 3.000 |
| White Mineral Oil | 0.500 |
| FD&C Yellow No. 5 1% solution | 0.001 |
| PVP/VA E 735 | 0.350 |
| Solulan 98 (Lanolin Acetate) | 0.200 |
| Formalin | 0.200 |
| Perfume | 0.300 |

(1)Active Ingredient (1) Active Ingredient

In preparing the hair shine conditioner of Example 1, the hydroxyethylcellulose is dispersed in one half of the formula amount of deionized water and mixed until a uniform clear solution is obtained and heated to 80-85 degrees C. with mixing. The yellow color solution, cetyl trimethyl ammonium chloride and citric acid are added to, and mixed with the aqueous hydroxyethyl cellulose solution at 80-85 degrees C. until a uniform aqueous solution is obtained. The cetyl alcohol, and mineral oil are slowly mixed and heated to 80-85 degrees C. in a small mixer until a uniform clear mixture is obtained, which is slowly added to, and mixed with the aqueous solution at 80-85 degrees C. After addition is completed, the rest of the water is added to the emulsion mixture with mixing which cools the mixture to about 50 degrees C. Polyvinylpyrrolidone/vinyl acetate and lanolin acetate are added to the emulsion at about 50 degrees C. with mixing and cooling the mixture to 39 degrees C. The perfume and formalin are added to the emulsion at 35-39 degrees C. with mixing and allowed to cool to room temperature. The final product is a yellow, smooth pourable lotion which is stable under all conditions of aging.

The composition of Example 1 is readily spreadable and distributes well throughout the hair when applied directly to the hair using the fingers. Also, wet and dry combing are very good and the treated hair has softness and body. Further, the hair is easily styled, and has a high shine. Maximum conditioning properties are obtained when the conditioner is applied to the hair without rinsing. Such use of this conditioner has application as a hair styling mousse.

EXAMPLES 2 & 3

| | HAIR CONDITIONER FOR DRY HAIR | |
| --- | --- | --- |
| Ingredients | 2 % | 3 % |
| Deionized Water - Irradiated | 48.000 | 45.890 |
| Natrosol - 250 HR[1] | 1.000 | 1.000 |
| Citric Acid - Anhy. | +/−0.010 | ÷/−.010 |
| FD&C Yellow No. 5 - 1% N.P. Soln. | +/−0.010 | — |
| 50% Cetyl Trimethyl Ammonium Chloride | 1.000 | — |
| 25% Cetyl Trimethyl Ammonium Chloride | — | 2.000 |
| Mineral Oil (Heavy) | 0.500 | 0.450 |
| Cetyl Alcohol | 3.000 | 3.000 |

HAIR CONDITIONER FOR DRY HAIR -continued

| Ingredients | 2 % | 3 % |
| --- | --- | --- |
| Deionized Water - Irradiated | 45.430 | 46.600 |
| Solulan 98 (Amerchol)[2] | 0.200 | 0.200 |
| PVP/VA E-735 (GAF) | 0.350 | 0.350 |
| Formalin | 0.200 | 0.200 |
| Perfume | 0.300 | 0.300 |

1. hydroxyethyl cellulose
2. lanolin acetate
pH "as is" (no citric acid added) 3.00 +/−0.30
Viscosity at 25 degrees C.
Brookfield RVTD
Spindle 5, Speed 10
After 1 Minute 10.000 +/−2,000 cps
Specific Gravity at 25 degrees C. 0.990 Minimum
Cetyl Trimethyl
Ammonium Chloride
Active 0.500 +/−0.050%

The shine hair conditioners for dry hair of Examples 2 and 3 are prepared by the method described in Example 1.

The final products provide excellant conditioning properties to dry hair including good combability, softness, manageability and a high shine.

EXAMPLES 4 AND 5

HAIR CONDITIONER FOR OILY HAIR

| Ingredients | 4 % | 5 % |
| --- | --- | --- |
| Natrosol 250HR | 1.000 | 1.000 |
| Deionized Water - Irradiated | 47.500 | 46.760 |
| Citric Acid - Anhy. | +/−0.010 | +/−0.100 |
| FD&C Yellow No. 5-1% N.P. Soln. | 0.010 | — |
| 50% Cetyl Trimethyl Ammonium Chloride | 0.750 | — |
| 25% Cetyl Trimethyl Ammonium Chloride | — | 1.5 |
| Cetyl Alcohol | 1.875 | 1.875 |
| Glyceryl Monostearate | 1.000 | 1.000 |
| Cyclomethicone (GE) | 0.500 | 0.500 |
| Deionized Water - Irradiated | 46.305 | 46.305 |
| Solulan 98 (Amerchol) | 0.200 | 0.200 |
| PVP/VA E-735 (GAF) | 0.350 | 0.350 |
| Formalin | 0.200 | 0.200 |
| Perfume | 0.300 | 0.300 |

Minimum Specific Gravity: 0.990
Viscosity: 10,000 cps +/−2000 cps

These compositions are prepared in accordance with the process of Ex. 1, except that the glyceryl monostearate replaces the mineral oil and the cyclomethicone is mixed with the cetyl alcohol and the glyceryl monostearate and heated to 80–85 degrees C. prior to addition of this mixture to the aqueous solution of hydroxyethyl cellulose and the cetyl trimethyl ammonium chloride at 80-85 degrees C.

The final product provides very good conditioning properties to oily hair including a high shine.

EXAMPLES 6 AND 7

HAIR CONDITIONER FOR NORMAL HAIR

| Ingredients | 6 % | 7 % |
| --- | --- | --- |
| Natrosol 250 HR | 1.000 | 1.000 |
| Deionized Water - Irradiated | 47.500 | 46.630 |
| Citric Acid - Anhy. | +/−0.010 | +/−0.010 |
| FD&C Yellow No. 5 - 1% N.P. Soln. | 0.010 | — |
| 50% Cetyl Trimethyl Ammonium Chloride | 0.880 | — |
| 25% Cetyl Trimethyl Ammonium Chloride | — | 1.760 |
| White Mineral Oil - Heavy | 0.450 | 0.450 |
| Cetyl Alcohol | 2.500 | 2.500 |
| Deionized Water - Irradiated | 46.600 | 46.600 |
| Solulan 98 (Amerchol) | 0.200 | 0.200 |
| PVP/VA E-735 (GAF) | 0.350 | 0.350 |
| Formalin | 0.200 | 0.200 |
| Perfume | 0.300 | 0.300 |

Specific Gravity: 0.990
Viscosity: 10,000 +/−2000 cps

Both compositions are prepared in accordance with the process of Example 1.

The final products provide conditioning properties to normal hair, particularly a high shine on the hair.

EXAMPLE 8

Another satisfactory shine conditioner for dry hair which is a stable lotion at temperatures of 24 degrees C. to 60 degrees C., is obtained when the mineral oil of Example 1 is increased to 0.65 percent, and the 0.2% lanolin acetate is replaced by 0.2% propylene glycol, and the water content is adjusted accordingly.

The wet combing properties of the shine conditioning rinse compositions of present invention are set forth in Table I below.

In the wet combing tests, tresses of virgin hair, 8–10 inches in length are shampooed with shampoo containing 10% SLES for one minute, rinsed with 40 degrees C. water for one minute, squeezed dry, treated with the test conditioners for one minute and rinsed with 40 degrees C. water for one minute. Thereafter, the tresses are combed while wet and rated for combability on a scale from one—the rating for hair which is shampooed only—to five—the rating for hair which is shampooed and treated with a good, effective rinse conditioner. This means that a rating of five indicates a good, effective conditioner, and a rating of one denotes a poor conditioner or shampoo wash. Thus, on the basis of these results the instant conditioner compositions are considered to be a good rinse conditioner. The results in Table I are the average of six readings and the combability tests were done by six combing experts.

TABLE I

| | Wet Combability Results | | | | |
| --- | --- | --- | --- | --- | --- |
| | Shampoo Control | Dry Ex. 2 | Normal Ex. 7 | Oily Ex. 4 | Conditioner Control |
| Avg. | 1.00 | 4.04 | 3.53 | 2.59 | 5.00 |

As indicated above, these results are obtained after one cycle, and one cycle is a shampoo treatment followed by a conditioner treatment. These results show that the dry hair conditioner has the best conditioning properties which is expected, because dry hair requires a conditioner containing a greater amount of conditioning agents than the normal hair conditioner, which in turn requires more conditioning agents than the oily hair conditioner.

In the dry combing tests, the pre-shampooed tresses are rinsed, squeezed dry and treated with the test conditioner for one minute, rinsed with 40 degrees C. water for one (1) minute and dried. The dried tresses are combed and rated for combability, similarly to the wet combing procedure. On the basis of these results, the instant conditioner compositions are considered to be good rinse conditioners as shown in Table II.

TABLE II

| | Dry Combability Results | | | |
|---|---|---|---|---|
| | Shampoo Control | Dry Ex. 2 | Normal Ex. 7 | Oily Ex. 4 | Conditioner Control |
| Avg. | 1 | 4.04 | 4.29 | 3.75 | 5 |

In the curl retention tests, tresses are washed with SLES based 10% shampoo, and the conditioners are applied as described in the dry combability test. The dried initial tresses are ten inches long. A curling iron is used to curl the hair tresses for 20 seconds, and the length after curlingn the tresses are measured and recorded. The length of the tresses after 16 hours are again measured and recorded. The increase in length of the treated tress after 16 hours is calculated and compated to the length increase of the control shampoo. From the data in Table III, it is concluded that the curl retention property, i.e. the holding property of the shine conditioners are greater than the prior art commercial conditioner, and the comparative Conditioner A, which does not contain three of the essential ingredients in the present shine conditioner, namely the cellulose polymer, the PVP/VA copolymer and the film plasticizer such as lanolin acetate. The A Conditioner contains the cetyl trimethyl ammonium chloride, cetyl alcohol, and mineral oil, but does not contain the film forming polymer ingredients and the plasticizer.

reading, the higher the shine on the surface of the hair. 1 is very shiny, 6 is very dull. The following tests were done to evaluate the Shine Conditioner:

(1) Shine Conditioner vs. Comparative Hair Conditioner A.
(2) Comparative Hair Conditioner A vs. Commercial Hair Conditioner C.
(3) Comparative Hair Conditioner A vs. Commercial Hair Conditioner D
(4) Comparative Hair Conditioner A vs. SLES Based Shampoo.

| Comparative Hair Conditioner A vs. Shine Conditioner | |
|---|---|
| AVG. 3.67 | 3.26 |
| Comparative Hair Conditioner A vs. Commer'l Hair Conditioner D. | |
| AVG. 2.80 | 4.48 |
| Comparative Hair Conditioner A vs. Commer'l Hair Conditioner C. | |
| AVG. 2.33 | 3.22 |
| Comparative Hair Conditioner A vs. SLES Based Shampoo | |
| AVG. 2.80 | 2.70 |

Therefore, the Shine Conditioner delivers more shine on the surface of the hair. Qualitative analysis has been performed using the light scattering instrument. Measurements are made on a single hair fiber held taut and irradiated with light incident at an angle that is prechosen and is measured with respect to the perpendicular to the fiber. The higher the reflected light (peak height) the shinier the hair. Individual hair fibers reflect light differently. Therefore a baseline peak height is established by treating the hair fiber with shampoo and taking its reflectance measurement. The test treatment (conditioner) is then applied and its reflectance curve

TABLE III

| | Curl Retention Test | | | | | | | | | |
|---|---|---|---|---|---|---|---|---|---|---|
| | SLES based Control Shampoo | Comparative Conditioner A | | Shine Cond. Oily Ex. 4 | | Shine Cond. Dry Ex. 2 | | Shine Cond. Normal Ex. 7 | | Commercial Cond. B Regular |
| Tresses | 1 | 1 | 2 | 1 | 2 | 1 | 2 | 1 | 2 | 1 | 2 |
| Initial Tresses Length Inches | 10" | 10" | 10" | 10" | 10" | 10" | 10" | 10" | 10" | 10" | 10" |
| Length After Curling the Tresses | 6⅜" | 6⅜" | 6⅛" | 6 6/8" | 6 6/8" | 7⅛" | 6⅜" | 6⅜" | 7 0/8" | 6⅜" | 6⅜" |
| Length After 16 Hours | 8⅞" | 8 2/8" | 8⅞" | 8 6/8" | 9 2/8" | 8 6/8" | 8 2/8" | 8 4/8" | 8 4/8" | 9 0/8" | 9 0/8" |
| Increase in Length | 2 4/8" | 1⅞" | 2 2/8" | 2 0/8" | 2 4/8" | 1⅝" | 1⅞" | 2⅛" | 1 4/8" | 2⅞" | 2⅞" |
| Compare to Control Length Decrease | — | −⅝" | −2/8" | −4/8" | — | −⅞" | −⅝" | −⅜" | −1 0/8" | −⅛" | −⅛" |
| Average Decrease in Length | — | −⅜" | | −2/8" | | −⅞" | | −6/8" | | −⅛" | |

The Shine Conditioner of the present invention has been shown, using a visual shine test and light scattering machine, to leave hair shinier than any other conditioner. The results are tabulated below:

Perceived luster is essentially a composite function of light scattering and light reflectance. When a beam of light strikes, part of the light will be reflected, part absorbed, and part scattered. This depends on the geometry of surface and the angle of the observer and the incidence of the light. A simple test was established comprising a method of keeping the light intensity constant and keeping the angle between the individual and object (tresses) constant. The equipment is made with a black background. Tresses are arranged in triplicate and 20 readings are taken for evaluation from 20 different people. The shine test rating evaluation was carried out and the average of 60 readings is listed. The lower the taken (Peak height). An increase or decrease in reflectance is shown by peak height. The shampoo base line indicates whether the treatment increased or decreased the luster or shine of the hair fiber.

The hair fiber is treated with 0.5 cc of shampoo and the fiber is placed on slides. The treatment is given for 30 seconds, then the fiber is washed out with 0.5 cc of tap water for 30 seconds. Reflectance measurement of the fiber is then taken. The fiber is then treated in the same manner for the measurement of the test samples (conditioner). The lower the percent peak height difference, the higher the shine rating.

The % height difference in Table IV measures the difference between the peak height of the shampooed fiber and the peak height of hair fiber shampooed with the test conditioner. The lower the peak height difference, the shinier the treated hair sample. The results of the data in Table IV clearly show that the shine conditioner of instant invention is shinier than the other hair conditioners.

TABLE IV

| | Light Scattering Data | | | | |
|---|---|---|---|---|---|
| | Shine Cond. | Comparative Hair Cond. A | Commercial Cond. B | Commercial Cond. D | Commercial Cond. C |
| % Height Diff | 13.75 | 23.59 | 25.51 | 51.71 | 58.53 |

It is understood that the foregoing detailed description is given merely by way of illustration and that variations may be made therein without departing from the spirit of the invention.

We claim:

1. A stable shine hair conditioner composition consisting essentially of about 0.375 tp 2.5% by weight of a $C_{14}-C_{22}$ alkyl trimethyl quaternary ammonium compound, about 0.25 to 2.5% by weight of a nonionic water soluble cellulose polymer, about 1 to 10% by weight of a $C_{14}-C_{22}$ alkanol, about 0.2 to 1.5% by weight mineral oil or glyceryl monostearate, about 0.1 to 1% by weight of a copolymer of polyvinyl pyrrolidone and vinyl acetate, and about 0.2 to 2% by weight of a plasticizer selected from the group consisting of lanolin acetate, water soluble lanolin, glycerine and propylene glycol, in about 80 to 97.5% by weight of an aqueous carrier, said composition being in the form of an emulsion and having a pH of about 2.5 to 5.5

2. A composition according to claim 1, wherein said quaternary compound is a cetyl trimethyl ammonium halide.

3. A composition according to claim 2, wherein said quaternary compound is cetyl trimethyl ammonium chloride.

4. A composition according to claim 1, wherein the $C_{14}-C_{22}$ alkanol is cetyl alcohol.

5. A composition according to claim 1, wherein said quaternary ammonium compound is a $C_{14}-C_{22}$ alkyl trimethyl ammonium halide and is present in the weight ratio of 1 to 5 with said alkanol.

6. A composition according to claim 1, wherein said cellulose polymer is hydroxyethyl cellulose and is present in an amount of about 0.25 to 2% by weight.

7. A composition according to claim 1, which is a conditioner for dry hair containing about 0.3 to 1% by weight of lanolin and about 0.2 to 1.5% by weight of the lanolin acetate plasticizer.

8. A composition according to claim 7, wherein the plasticizer is propylene glycol.

9. A composition according to claim 1, which is a conditioner for normal hair containing about 0.3 to 1% by weight of lanolin and 0.2 to 1.5% by weight of the lanolin acetate plasticizer.

10. A shine conditioner for dry hair according to claim 1, consisting essentially of hydroxyethyl cellulose about 0.5% by weight of cetyl trimethyl ammonium chloride, about 0.5% by weight of mineral oil, about 3% by weight of cetyl alcohol, lanolin acetate, and the polyvinyl pyrrolidone/vinyl acetate copolymer in about 90 to 95% by weight of deionized water.

11. A shine conditioner for normal hair according to claim 1, consisting essentially of hydroxyethyl cellulose, about 0.44% by weight of cetyl trimethyl ammonium chloride, about 2.5% by weight of cetyl alcohol; about 0.45% by weight of mineral oil, lanolin acetate, and polyvinyl pyrrolidone/vinyl acetate copolymer, in about 90 to 95% by weight of deionized water.

12. A stable shine hair conditioner composition consisting essentially of about 0.375 to 2.5% by weight of a $C_{14}-C_{22}$ alkyl trimethyl quaternary ammonium compound, about 0.25 to 2.5% by weight of a nonionic water soluble cellulose polymer, about 1 to 10% by weight of a $C_{14}-C_{22}$ alkanol, about 0.2 to 1.5% by weight mineral oil or glyceryl monostearate, about 0.1 to 1% by weight of a copolymer of polyvinyl pyrrolidone and vinyl acetate, about 0.2 to 2% by weight of cyclomethicone, and about 0.2 to 2% by weight of a plasticizer selected from the group consisting of lanolin acetate, water soluble lanolin, glycerine and propylene glycol, in about 80 to 97.5% by weight of an aqueous carrier, said composition being in the form of an emulsion and having a pH of about 2.5 to 5.5.

13. A composition according to claim 12, which is a hair conditioner for oily hair containing about 0.3 to 1% by weight glyceryl monostearate and about 0.2 to 1% by weight of cyclomethicone.

14. An shine conditioner for oily hair according to claim 12, consisting essentially of hydroxyethyl cellulose, about 0.375% by weight of cetyl trimethyl ammonium chloride, about 1.875% by weight of cetyl alcohol, about 1% by weight of glyceryl monostearate, about 0.5% by weight of cyclomethicone, lanolin acetate, and the copolymer of polyvinyl pyrrolidone and vinyl acetate in about 90 to 95% by weight of deionized water.

* * * * *